US00PP19878P2

(12) United States Plant Patent
Mathis

(10) Patent No.: US PP19,878 P2
(45) Date of Patent: Mar. 31, 2009

(54) ORCHID PLANT NAMED 'KATE'

(50) Latin Name: *Bletilla Yokohama (B. striata ×B. formosana*
Varietal Denomination: Kate

(75) Inventor: William D. Mathis, Doylestown, PA (US)

(73) Assignee: Mathis Family Enterprises, LLC., Doylestown, PA (US)

( * ) Notice: Subject to any disclaimer, the term of this patent is extended or adjusted under 35 U.S.C. 154(b) by 0 days.

(21) Appl. No.: 12/069,523

(22) Filed: Feb. 11, 2008

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para
*Assistant Examiner*—S. B. McCormick Ewoldt
(74) *Attorney, Agent, or Firm*—Jondle & Associates, P.C.

(57) ABSTRACT

A new Orchid plant particularly distinguished by having pale-lavender flowers, double branched inflorescences, a long scape and flower sepals and petals that open wide and erect, is disclosed.

3 Drawing Sheets

Genus and species: *Bletilla* Yokohama (*B. striata×B. formosana*).
Variety denomination:

BACKGROUND OF THE NEW PLANT

The present invention comprises a new and distinct cultivar of terrestrial orchid, botanically known as *Bletilla* Yokohama (*B. striata×B. formosana*), and hereinafter referred to by the cultivar name 'Kate'. 'Kate' was produced by crossing *Bletilla striata* 'Big Bob' (unpatented) as the pod parent and pollen from an unknown individual plant of *Bletilla formosana.*

The new cultivar was created in June 2001, in Doylestown, Pa. and has been asexually reproduced repeatedly by vegetative bulb separation (division) and tissue culture for 2.5 years. The present invention has been found to retain its distinctive characteristics through successive asexual propagations.

SUMMARY OF THE INVENTION

The following are the most outstanding and distinguishing characeristics of this new cultivar when grown under normal horticultural practices in Doylestown, Pa.

a. Pale-lavender flowers;

b. Double branched inflorescences;

c. A long scape; and d. Flower sepals and petals that open very wide and erect.

DESCRIPTION OF THE PHOTOGRAPHS

This new orchid plant is illustrated by the accompanying photographs which show overall plant habit including blooms, buds, and foliage of the plant; the colors shown are as true as can be reasonably obtained by conventional photographic procedures. The photographs are of plants that are 5 years old.

DESCRIPTION OF THE NEW CULTIVAR

Figure 1:
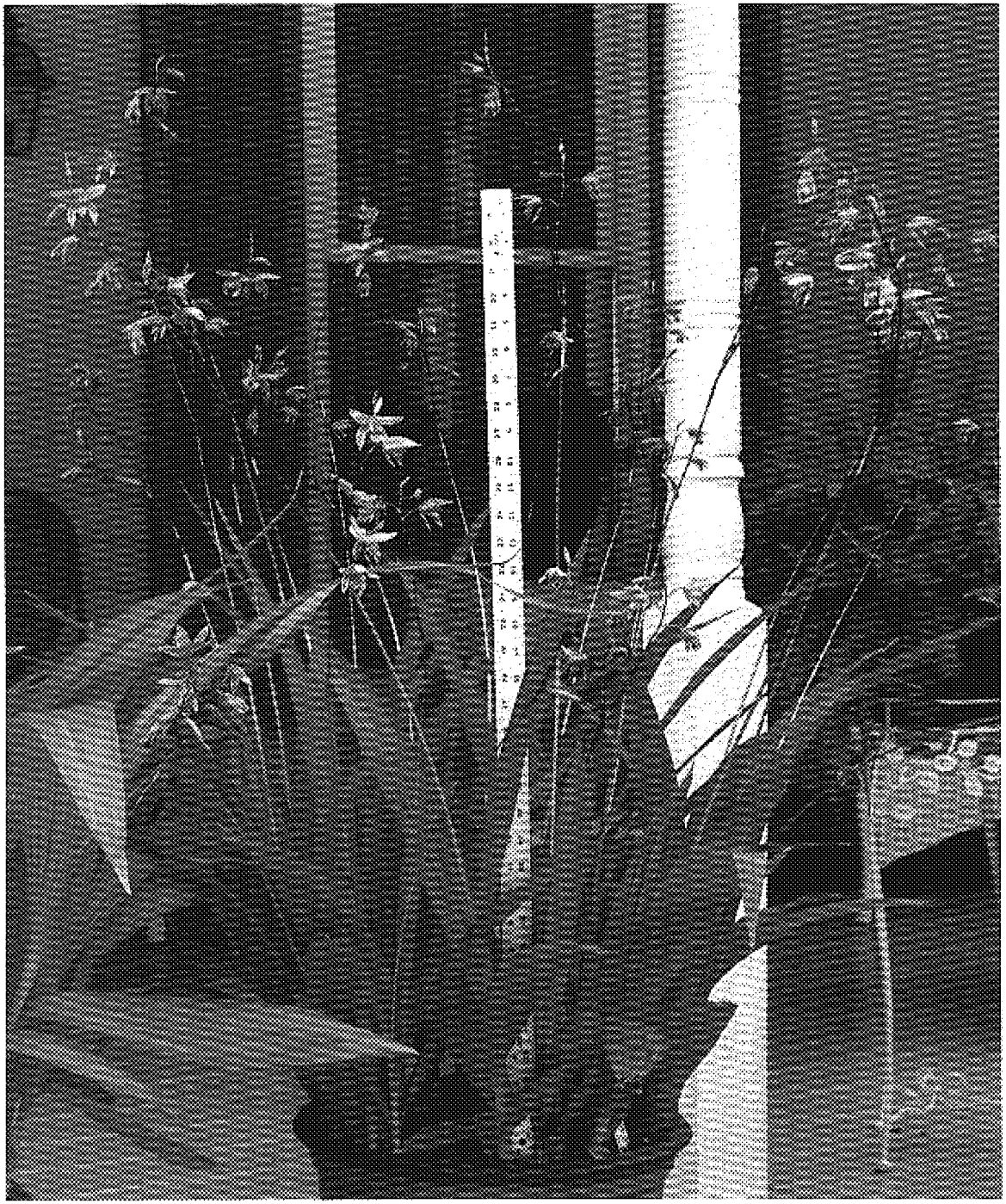
FIG. 1 shows overall plant habit including blooms, buds and foliage.
Figure 2:
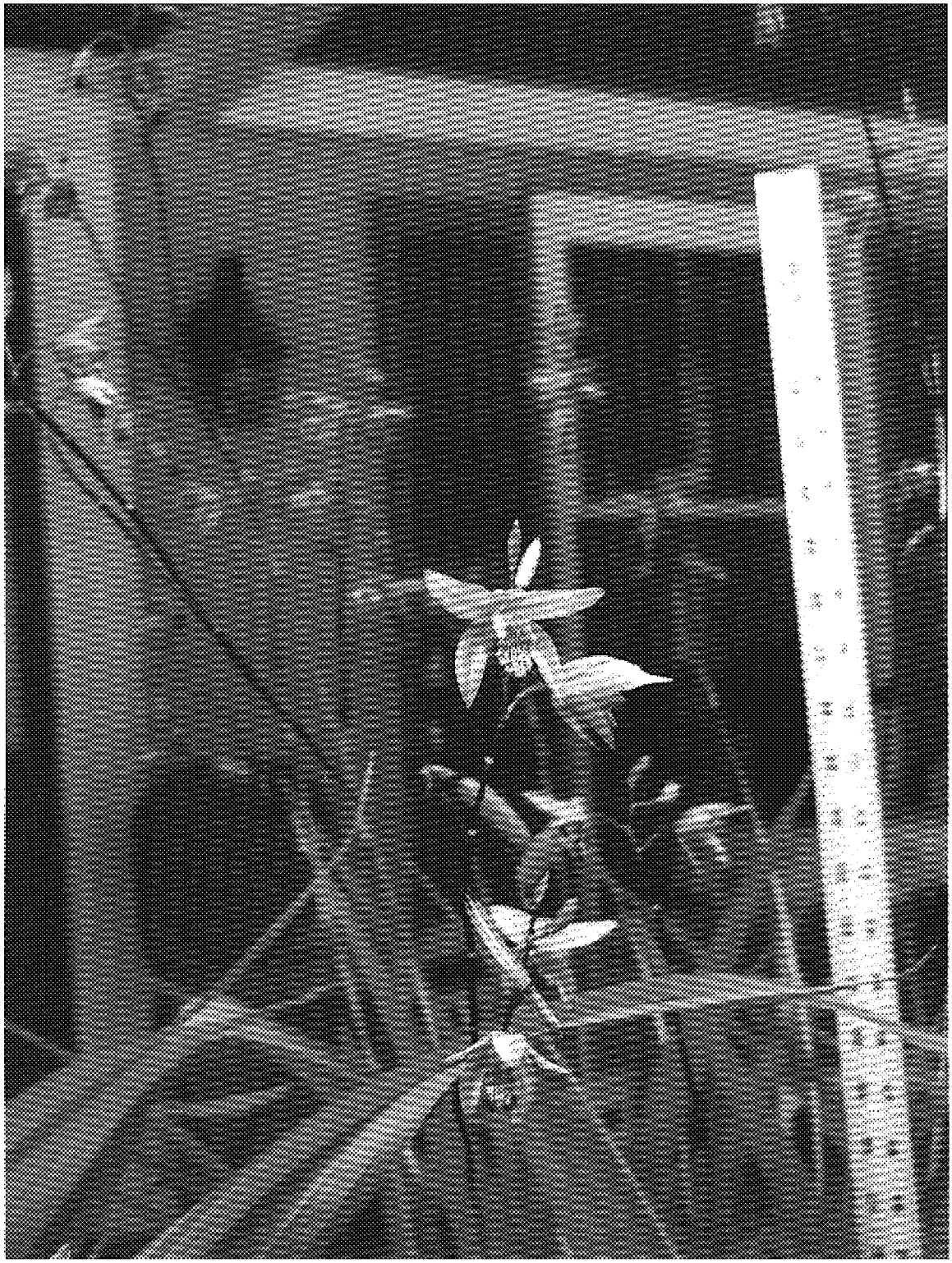
FIG. 2 shows the mature inflorescence.
Figure 3:
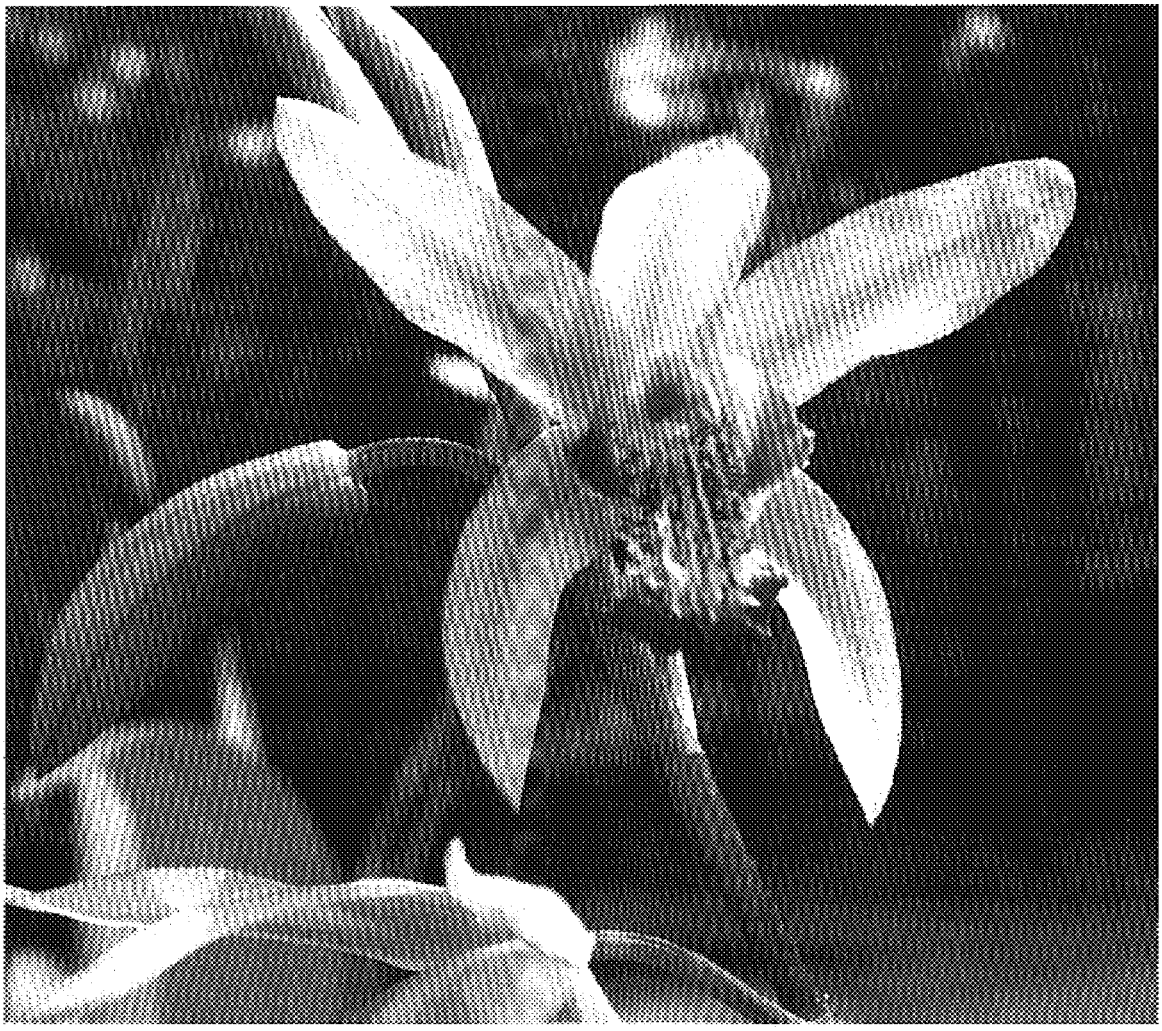
FIG. 3 shows a close-up of the mature inflorescence.

The following detailed descriptions set forth the distinctive characteristics of 'Kate'. The data which define these characteristics were collected from bulb divisions carried out in Doylestown, Pa. The plant history was taken on plants grown for about 6 years in raised beds and 14 inch pots under field conditions with natural light during May to October. Color references primarily to the R.H.S. Colour Chart of The Royal Horticultural Society of London (R.H.S.), 5$^{th}$ edition (2007).

DETAILED BOTANICAL DESCRIPTION

Classification:

*Botanical.*—*Bletilla* Yokohama (*B. striata× formosana*).

*Common name.*—Orchid.

Parentage: Produced by crossing *Bletilla striata* 'Big Bob' (unpatented) as the pod parent and pollen from an unknown individual plant of *B. formosana.*

Plant:

*Propagation.*—Vegetative bulb divisions and tissue culture.

*Mature plant size.*—Height: 50 to 60 cm. Diameter: 20 to 30 cm. Height of mature plant with inflorescence: About 110 cm.

*Growth habit description.*—A hardy perennial that requires a dormant period for best growth. It starts blooming in the second year out of flask and will bloom every year there after under good growing conditions. The inflorescence gets larger with more flowers as the pseudobulb matures which takes a year under good growing conditions and cultural practices. After the initial psuedobuilb matures it will produce one or more new psuedobulb per growing season there after. It blooms once a year starting in late Spring (June) continuing into Summer (August) months.

*Vigor.*—very vigorous when grown in full sun; seedlings start to bloom at least one year earlier than either parent.

*Growing conditions.*—Soil mix of 50% sand, 50% composted leaves or any good moisture retentive, high fertility garden soil mix with a pH range from 6 to 7.5.

*Flowering time.*—May to June; zone dependant.

*Flowering period.*—6 to 8 weeks.

*Lastingness of flowers on the plant.*—Generally one or two flower open at a time; individual flowers last 5 to 7 days.

Leaves:

*Leaf blade.*—The sheathing leaf bases forms a pseudostem which is about 20 to 30 cm in length; there are three to five leaves that are articulated to the sheaths; thin-textured, deciduous and conspicuously pleated.

*Quantity.*—Usually five sheathed together with a scape emerging from the last leaf.

*Arrangement.*—sheathed in whorl around the scape.

*Mature leaf length.*—45.72 cm to 60.96 cm.

*Mature leaf width at base.*—3.81 cm to 5.1 cm.

*Shape.*—Lancelet.

*Apex.*—Acute.

*Base.*—Sheathing leaf bases form a pseudostem with 3 to 5 leaves articulated to the sheath.

*Margin.*—Entire.

*Color*—Upper leaf surface: RHS 146A (dark-green); same color for base, apex and margin of upper leaf surface. Lower leaf surface: RHS 146A (dark-green); same color for base, apex and margin of lower leaf surface.

Flowers:

*General.*—Petals are oblanceolate, slightly narrowed to the base, and obtuse, while the sepals are less narrowed and the apex is acute; the lateral sepals are distinctly falcate.

*Flower diameter.*—5.1 cm.

*Variegation.*—None.

*Number of scapes per shoot.*—One.

*Inflorescence length* (*from base to tip*).—110 cm.

*Flowers per stem* (*per scape*).—Up to 35.

*Petals* (*lateral petals*).—Number: 2 plus labellum. Shape: Oblanceolate. Length: 3.0 cm to 4.0 cm. Width: 1.0 cm at base. Color (both surfaces): RHS 73D (pale-lavender) with RHS 73B (dark purple-red) mid-veins.

*Sepals.*—Number: 3. Shape: Lower (lateral): Falcate. Upper: Oblanceolate. Length: 3.0 cm. Width: 0.75 cm to 1.0 cm. Color (both surfaces): RHS 73D (pale-lavender) with RHS 73B. (dark purple-red) mid-veins.

*Labellum or lip.*—General: The labellum is distinctly three-lobed. The 2 lateral lobes of the labellum closely embrace the column and conspicuously exceed it in length. The apices of the lateral lobes are RHS 72B (dark-purple), crenulate and slightly ruffled. The midlobe is somewhat orbicular, with the margin, crenulate and distinctly ruffled. The midlobe apex is RHS 72B (dark-purple) and deeply but narrowly notched. The five crests (or lamellae), are RHS 9A (yellow) toward the front and becoming RHS NN155D (white) to the rear with RHS 45A (deep-red) spots, smooth but conspicuously undulate only on the midlobe, becoming of lower relief and not undulate beyond the midlobe toward the front of the lip. Arrangement: Resupinate. Width: 1.5 cm. Length (including base): 2.5 cm. Color: Upper labellum surface: Midlobe of the lip with RHS 9A (bright-yellow) surrounding the callus with RHS 45A (deep-red) blotches; front margin rounded and darker-purple. Lower labellum surface: RHS 62A (very light-purple).

*Fragrance.*—None detectable.

*Pedicel.*—Length: 0.5 cm to 0.75 cm. Diameter: 0.2 cm. Color: Early flowering cycle (1 to 2 weeks): RHS 146D (light-green). Later flowering cycle (3 to 6 weeks): RHS 65A (reddish).

Scape: Length: 110 cm. Diameter 2.0 cm. Color: Early flowering cycle (1 to 2 weeks): RHS 146D (light-green). Later flowering cycle (3 to 6 weeks): RHS 65A (reddish).

*Texture.*—Smooth.

*Number of flowers per scape.*—At least 35.

*Number of branches per scape.*—Most commonly 2 to 3 branches.

Roots:

*General description.*—Pseudobulbs produce a large mass of fairly fine white (RHS NN155C), fleshy roots; one pseudobulb initiates about 50 roots, and these divide into branches.

*Diameter.*—0.1 cm.

*Color.*—RHS NN155C (white).

Pseudobulbs:

*General.*—Plants grow from large fleshy, compressed pseudobulbs, often referred to as "corms".

*Diameter.*—6.0 cm to 8.0 cm.

*Thickness.*—4.0 cm to 5.0 cm.

*Color.*—RHS 165D (light-brown) to RHS 165A (tan).

*Texture.*—Smooth with sometimes russeting.

Reproductive organs:

*General.*—The stamens, style and stigmas are fused into a single short structure called the column, possessing one terminal anther with pollen grains united into a pollinia, which are covered by an anther cap; the stigma is located under the column behind the pollinia; ovary inferior, three carples present. The column is slightly arched, narrowly winged on both sides and without a foot. The eight pollinia form two groups and are granular, with an inconspicuous caudicle, and without a viscidium.

*Column.*—Length: About 2 cm. Width: About 0.6 cm. Color: RHS 73D (pale-lavender) with RHS 72A (darker purple) at the apex.

*Stigma color.*—RHS 73D (pale-lavender).

*Pollinia.*—Number: Eight pollinia form two groups. Diameter: About 0.1 cm. Shape: Irregular. Color: RHS 3A (yellow).

*Ovary.*—Length: 0.5 cm. Diameter: 0.2 cm.

Fruit and Seed Set: The fusiform capsules are about 5 cm in length. At maturity the capsules incompletely open, thus reluctant to shed seeds. Open pollination is common and the seeds are viable. The seeds consist of an outer cover or testa which is 1.0 to 1.5 mm long and about 0.1 mm wide, RHS 158D (light tan) color and an inner immature embryo which is 0.09 mm in diameter and RHS 158B (tan) in color.

Disease and Insect resistance: No particular resistance or susceptibility has been observed.

COMPARISON WITH PARENTAL AND COMMERCIAL CULTIVARS

'Kate' differs from the parental variety 'Big Bob' (unpatented) in that 'Kate' has triple branched inflorescences with a scape of about 110 cm in length, with about 35 flowers per inflorescence, while 'Big Bob' has occasional single branching inflorescences with a scape of about 90 cm in length and about 20 flowers per inflorescence. In addition, 'Kate' has a yellow (RHS 9A) lip color, while, 'Big Bob' has a white (RHS NN155C) lip color.

'Kate' differs from the unknown individual *Bletilla formosana* plant (the pollen donator) in that 'Kate' has triple branched inflorescences with a scape of about 110 cm in length, with about 35 flowers per inflorescence, while the unknown individual *Bletilla formosana* plant occasionally has single branched inflorescences with a scape of less than 60 cm in length and 10 to 15 flowers per inflorescence. In addition, 'Kate' has a larger flower diameter of 5 cm and opens widely compared to the unknown individual *Bletilla formosana* plant which has a flower diameter around 1.5 cm and does not open as fully.

'Kate' differs from the *Bletilla* Yokohama plant (registered by K. Suzuki in 1956 with The Royal Horticultural Society, produced from the cross of a *Bletilla striata*× *Bletilla formosana*) in that 'Kate' has a scape of about 110 cm in length, about 35 flowers per scape and flowers that are 5 cm in diameter that open fully, while the *Bletilla* Yokohama cultivar has scapes that are less than 60 cm in length, less than 15 flowers per scape and flowers that are 3 cm in diameter and tend not to open fully. In addition, 'Kate' has triple branched inflorescences, while the *Bletilla* Yokohama cultivar usually have no branching of infloresences (sometimes one branch, but never more than one).

I claim:

1. A new and distinct cultivar of Orchid plant as shown and described herein.

* * * * *